United States Patent
Zhao (10) Patent No.: US 11,385,126 B2
(45) Date of Patent: Jul. 12, 2022

(54) METHODS AND SYSTEMS FOR MEASURING IMAGE QUALITY

(71) Applicant: Johnson & Johnson Surgical Vision, Inc., Irvine, CA (US)

(72) Inventor: Huawei Zhao, Saint Augustine, FL (US)

(73) Assignee: Johnson & Johnson Surgical Vision, Inc., Irvine, CA (US)

(*) Notice: Subject to any disclaimer, the term of this patent is extended or adjusted under 35 U.S.C. 154(b) by 12 days.

(21) Appl. No.: 16/987,345

(22) Filed: Aug. 6, 2020

(65) Prior Publication Data

US 2020/0396387 A1 Dec. 17, 2020

Related U.S. Application Data

(62) Division of application No. 15/927,518, filed on Mar. 21, 2018, now Pat. No. 10,739,227.

(Continued)

(51) Int. Cl.
*H04N 5/232* (2006.01)
*G01M 11/02* (2006.01)
(Continued)

(52) U.S. Cl.
CPC ....... *G01M 11/0257* (2013.01); *A61F 2/1637* (2013.01); *G01M 11/0292* (2013.01);
(Continued)

(58) Field of Classification Search
CPC ..... A61F 2/1637; G02C 7/02; G02C 2202/02; G01M 11/0292; G01M 11/0257; H04N 5/2254; H04N 5/372
See application file for complete search history.

(56) References Cited

U.S. PATENT DOCUMENTS 2,077,092 A   4/1937   Broder
3,305,294 A   2/1967   Alvarez
(Continued)

FOREIGN PATENT DOCUMENTS

DE   8107675 U1   7/1981
DE   102005022683 A1   11/2006
(Continued)

OTHER PUBLICATIONS

Abelman H., et al. "Tolerance and Nature of Residual Refraction in Symmetric Power Space as Principal Lens Powers and Meridians Change," Computational and Mathematical Methods in Medicine, Article ID 492383, 2014, vol. 2014, pp. 1-12.
(Continued)

*Primary Examiner* — Sang H Nguyen
(74) *Attorney, Agent, or Firm* — Johnson & Johnson Surgical Vision, Inc.

(57) ABSTRACT

Methods and systems for measuring the asymmetrical image quality or image features of an intraocular lens (IOL), design, refractive and diffractive designs, such as IOLs with Extended tolerance of astigmatic effects are provided by through-focus and meridian response. Measurements are taken at various focal plane and meridian positions to allow for determination of areas of better performance away from 0 meridian or the start position and meridian.

11 Claims, 7 Drawing Sheets

Related U.S. Application Data (60) Provisional application No. 62/475,778, filed on Mar. 23, 2017.

(51) Int. Cl.
*H04N 5/225* (2006.01)
*H04N 5/372* (2011.01)
*G02C 7/02* (2006.01)
*A61F 2/16* (2006.01)

(52) U.S. Cl.
CPC ............ *G02C 7/02* (2013.01); *H04N 5/2254* (2013.01); *H04N 5/23299* (2018.08); *H04N 5/372* (2013.01); *A61F 2/16* (2013.01); *G02C 2202/02* (2013.01)

(56) References Cited

U.S. PATENT DOCUMENTS

| | | |
|---|---|---|
| 3,367,734 A | 2/1968 | Karl et al. |
| 3,735,685 A | 5/1973 | Plummer |
| 4,010,496 A | 3/1977 | Neefe |
| 4,056,311 A | 11/1977 | Winthrop |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen et al. |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen |
| 4,370,760 A | 2/1983 | Kelman |
| 4,377,873 A | 3/1983 | Reichert, Jr. |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,437,733 A | 3/1984 | Takahashi et al. |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,637,697 A | 1/1987 | Freeman |
| 4,642,112 A | 2/1987 | Freeman |
| 4,655,565 A | 4/1987 | Freeman |
| 4,665,913 A | 5/1987 | L'Esperance, Jr. |
| 4,669,466 A | 6/1987 | L'Esperance |
| 4,673,406 A | 6/1987 | Schlegel |
| 4,676,791 A | 6/1987 | Lemaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,732,148 A | 3/1988 | L'Esperance, Jr. |
| 4,734,095 A | 3/1988 | Siepser |
| 4,764,930 A | 8/1988 | Bille et al. |
| 4,770,172 A | 9/1988 | L'Esperance, Jr. |
| 4,773,414 A | 9/1988 | L'Esperance, Jr. |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,261 A | 9/1989 | Flammer |
| 4,863,539 A | 9/1989 | Lee et al. |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,042,938 A | 8/1991 | Shimozono |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,108,388 A | 4/1992 | Trokel et al. |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,163,934 A | 11/1992 | Munnerlyn |
| 5,173,723 A | 12/1992 | Volk et al. |
| 5,184,405 A | 2/1993 | Cress |
| 5,191,187 A * | 3/1993 | Kajikawa ............... B23K 26/04 219/121.76 |
| 5,197,981 A | 3/1993 | Southard |
| 5,201,763 A | 4/1993 | Brady et al. |
| 5,203,790 A | 4/1993 | McDonald |
| 5,207,668 A | 5/1993 | L'Esperance, Jr. |
| 5,217,491 A | 6/1993 | Vanderbilt |
| 5,219,343 A | 6/1993 | L'Esperance, Jr. |
| 5,225,858 A | 7/1993 | Portney |
| 5,229,797 A | 7/1993 | Futhey et al. |
| 5,258,025 A | 11/1993 | Fedorov et al. |
| 5,278,592 A | 1/1994 | Marie et al. |
| 5,379,110 A | 1/1995 | Matsui et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,646,791 A | 7/1997 | Glockler |
| 5,652,638 A | 7/1997 | Roffman et al. |
| 5,652,640 A | 7/1997 | Schneider et al. |
| 5,691,800 A | 11/1997 | Iki et al. |
| 5,699,142 A | 12/1997 | Lee et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 5,993,438 A | 11/1999 | Juhasz et al. |
| 6,015,435 A | 1/2000 | Valunin et al. |
| 6,051,024 A | 4/2000 | Cumming |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |

(56) References Cited

U.S. PATENT DOCUMENTS

| | | |
|---|---|---|
| 6,210,005 B1 | 4/2001 | Portney |
| 6,235,055 B1 | 5/2001 | Chu |
| 6,241,356 B1 | 6/2001 | Von et al. |
| 6,261,321 B1 | 7/2001 | Kellan |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,460,997 B1 | 10/2002 | Frey et al. |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,497,483 B2 | 12/2002 | Frey et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,550,917 B1 | 4/2003 | Neal et al. |
| 6,554,859 B1 | 4/2003 | Lang et al. |
| 6,557,992 B1 | 5/2003 | Dwyer et al. |
| 6,575,572 B2 | 6/2003 | Lai et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,786,603 B2 | 9/2004 | Altmann |
| 6,802,605 B2 | 10/2004 | Cox et al. |
| 6,808,262 B2 | 10/2004 | Chapoy et al. |
| 6,817,714 B2 | 11/2004 | Altmann |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,281,797 B2 | 10/2007 | Yamaguchi et al. |
| 7,287,852 B2 | 10/2007 | Fiala |
| 7,293,873 B2 | 11/2007 | Dai et al. |
| 7,296,893 B2 | 11/2007 | Dai |
| 7,339,539 B2 | 3/2008 | Joannopoulos et al. |
| 7,350,916 B2 | 4/2008 | Hong et al. |
| 7,365,917 B2 | 4/2008 | Zalevsky |
| 7,377,640 B2 | 5/2008 | Piers et al. |
| 7,425,068 B2 * | 9/2008 | Koest .................... A61B 3/117 351/246 |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,547,102 B2 | 6/2009 | Dai |
| 7,615,073 B2 | 11/2009 | Deacon et al. |
| 7,616,330 B2 | 11/2009 | Neal et al. |
| 7,659,971 B2 | 2/2010 | Warden et al. |
| 7,726,813 B2 | 6/2010 | Dai |
| 7,784,946 B2 | 8/2010 | Leblanc |
| 7,794,497 B2 | 9/2010 | Brady et al. |
| 7,857,451 B2 | 12/2010 | Thibos et al. |
| 7,871,162 B2 | 1/2011 | Weeber |
| 7,911,211 B2 | 3/2011 | Crain et al. |
| 7,931,371 B2 | 4/2011 | Dai |
| 7,931,374 B2 | 4/2011 | Dai et al. |
| 7,938,538 B2 | 5/2011 | Lu et al. |
| 7,944,553 B1 | 5/2011 | Simpson et al. |
| 7,969,585 B2 | 6/2011 | Neal et al. |
| 8,123,357 B2 | 2/2012 | Dai et al. |
| 8,382,281 B2 | 2/2013 | Weeber |
| 8,480,228 B2 | 7/2013 | Weeber |
| 8,596,787 B2 | 12/2013 | Dai |
| 8,657,445 B2 | 2/2014 | Olsen |
| 8,696,119 B2 | 4/2014 | Van et al. |
| 8,740,382 B1 | 6/2014 | Liu et al. |
| 8,746,882 B2 | 6/2014 | Canovas et al. |
| 8,764,822 B2 | 7/2014 | Harris et al. |
| 8,862,447 B2 | 10/2014 | Weeber |
| 9,211,061 B2 | 12/2015 | Kasthurirangan et al. |
| 9,241,627 B2 | 1/2016 | Steinmueller |
| 9,393,108 B2 | 7/2016 | Canovas et al. |
| 9,491,431 B2 | 11/2016 | Zhou |
| 9,700,201 B2 | 7/2017 | Bex et al. |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0033013 A1 | 2/2003 | Callahan et al. |
| 2003/0053025 A1 | 3/2003 | Turner et al. |
| 2003/0076478 A1 | 4/2003 | Cox |
| 2003/0163122 A1 | 8/2003 | Sumiya |
| 2003/0171808 A1 | 9/2003 | Phillips |
| 2003/0189690 A1 | 10/2003 | Mihashi et al. |
| 2004/0021825 A1 | 2/2004 | Richardson |
| 2004/0054358 A1 | 3/2004 | Cox et al. |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0156014 A1 | 8/2004 | Piers et al. |
| 2004/0167622 A1 | 8/2004 | Sunalp et al. |
| 2004/0183997 A1 | 9/2004 | Suzuki |
| 2004/0260275 A1 | 12/2004 | Liang et al. |
| 2005/0024647 A1 | 2/2005 | Montgomery |
| 2005/0096226 A1 | 5/2005 | Stock et al. |
| 2005/0122474 A1 | 6/2005 | Koretz |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0055877 A1 | 3/2006 | Yanari |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0203198 A1 | 9/2006 | Liang |
| 2006/0238702 A1 | 10/2006 | Glick et al. |
| 2006/0244906 A1 | 11/2006 | Piers et al. |
| 2006/0244916 A1 | 11/2006 | Guillon |
| 2006/0274268 A1 | 12/2006 | Andino et al. |
| 2006/0279699 A1 | 12/2006 | Liang |
| 2006/0279700 A1 | 12/2006 | Liang |
| 2007/0052920 A1 | 3/2007 | Stewart et al. |
| 2007/0052927 A1 | 3/2007 | Noda et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0195265 A1 | 8/2007 | Dreher et al. |
| 2007/0268453 A1 | 11/2007 | Hong et al. |
| 2007/0285617 A1 | 12/2007 | Mills et al. |
| 2008/0018910 A1 | 1/2008 | Neal et al. |
| 2008/0030677 A1 | 2/2008 | Simpson |
| 2008/0033546 A1 | 2/2008 | Liang |
| 2008/0161913 A1 | 7/2008 | Brady et al. |
| 2008/0161914 A1 | 7/2008 | Brady et al. |
| 2008/0198331 A1 | 8/2008 | Azar et al. |
| 2008/0231809 A1 | 9/2008 | Haigis |
| 2008/0269642 A1 | 10/2008 | Deacon et al. |
| 2008/0273169 A1 | 11/2008 | Blum et al. |
| 2008/0291393 A1 | 11/2008 | Menezes |
| 2009/0000628 A1 | 1/2009 | Somani et al. |
| 2009/0012609 A1 | 1/2009 | Geraghty et al. |
| 2009/0036980 A1 | 2/2009 | Norrby et al. |

(56) References Cited

U.S. PATENT DOCUMENTS

| | | |
|---|---|---|
| 2009/0062911 A1 | 3/2009 | Bogaert |
| 2009/0067940 A1* | 3/2009 | Arai .................. B24B 9/14 |
| | | 408/22 |
| 2009/0164008 A1 | 6/2009 | Hong et al. |
| 2009/0168019 A1 | 7/2009 | Tuan |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0275929 A1 | 11/2009 | Zickler |
| 2009/0279048 A1 | 11/2009 | Hong et al. |
| 2009/0281552 A1 | 11/2009 | Hiramatsu et al. |
| 2009/0292354 A1 | 11/2009 | Gontijo et al. |
| 2009/0295295 A1 | 12/2009 | Shannon et al. |
| 2009/0303465 A1 | 12/2009 | Clements et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0097569 A1 | 4/2010 | Weeber et al. |
| 2010/0097619 A1* | 4/2010 | Ge .................. G01M 11/0271 |
| | | 356/511 |
| 2010/0130888 A1 | 5/2010 | Deacon et al. |
| 2010/0161048 A1 | 6/2010 | Schaper, Jr. |
| 2010/0179793 A1 | 7/2010 | Chernyak et al. |
| 2010/0220185 A1 | 9/2010 | Vertoprakhov et al. |
| 2010/0234833 A1 | 9/2010 | Dai |
| 2010/0315589 A1 | 12/2010 | Portney |
| 2011/0080562 A1 | 4/2011 | Iizuka et al. |
| 2011/0149236 A1 | 6/2011 | Weeber |
| 2011/0166652 A1 | 7/2011 | Bogaert et al. |
| 2011/0205486 A1 | 8/2011 | Zhao |
| 2011/0211163 A1 | 9/2011 | Meuse et al. |
| 2012/0140166 A1 | 6/2012 | Zhao |
| 2012/0168605 A1* | 7/2012 | Milanovic .......... G01B 11/002 |
| | | 250/203.1 |
| 2012/0238904 A1 | 9/2012 | Manns et al. |
| 2012/0249955 A1 | 10/2012 | Sarver et al. |
| 2012/0310337 A1 | 12/2012 | Hacker et al. |
| 2013/0050637 A1 | 2/2013 | Roffman et al. |
| 2013/0226294 A1 | 8/2013 | Van et al. |
| 2013/0307965 A1 | 11/2013 | Widman et al. |
| 2013/0314669 A1 | 11/2013 | Levin et al. |
| 2013/0345807 A1 | 12/2013 | Olsen et al. |
| 2014/0016088 A1 | 1/2014 | De et al. |
| 2014/0135919 A1 | 5/2014 | Gontijo et al. |
| 2014/0176904 A1 | 6/2014 | Lai |
| 2014/0268042 A1 | 9/2014 | Bor et al. |
| 2014/0293426 A1 | 10/2014 | Dobschal |
| 2014/0320805 A1 | 10/2014 | Wilzbach et al. |
| 2015/0062529 A1 | 3/2015 | Kasthurirangan et al. |
| 2015/0138350 A1 | 5/2015 | Videcoq |
| 2015/0250583 A1 | 9/2015 | Rosen et al. |
| 2015/0320547 A1 | 11/2015 | Rosen et al. |
| 2015/0359625 A1 | 12/2015 | Argal et al. |
| 2015/0362746 A1 | 12/2015 | Skudder et al. |
| 2015/0379348 A1 | 12/2015 | Whritenor et al. |
| 2016/0157997 A1 | 6/2016 | Gerlach et al. |
| 2016/0161364 A1 | 6/2016 | Alarcon Heredia et al. |
| 2016/0299355 A1 | 10/2016 | Biemold et al. |
| 2016/0335474 A1 | 11/2016 | Santos-Villalobos et al. |
| 2017/0189233 A1 | 7/2017 | Dewey et al. |

FOREIGN PATENT DOCUMENTS

| | | |
|---|---|---|
| EP | 226400 A2 | 6/1987 |
| EP | 227357 A2 | 7/1987 |
| EP | 0538126 B1 | 9/1996 |
| EP | 0810427 A1 | 12/1997 |
| EP | 0926531 A1 | 6/1999 |
| EP | 957331 A2 | 11/1999 |
| EP | 1310267 B1 | 1/2008 |
| EP | 2631891 A1 | 8/2013 |
| EP | 3059575 A1 | 8/2016 |
| FR | 2745711 A1 | 9/1997 |
| GB | 2433782 A | 7/2007 |
| GB | 2488802 A | 9/2012 |
| WO | 8603961 A1 | 7/1986 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 9905499 A1 | 2/1999 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0185016 A2 | 11/2001 |
| WO | 0189424 A1 | 11/2001 |
| WO | 0221194 A2 | 3/2002 |
| WO | 02074210 A2 | 9/2002 |
| WO | 03009053 A1 | 1/2003 |
| WO | 04028356 A1 | 4/2004 |
| WO | 2004034129 A1 | 4/2004 |
| WO | 2004053568 A1 | 6/2004 |
| WO | 2004079637 A1 | 9/2004 |
| WO | 2004090611 A2 | 10/2004 |
| WO | 2004096014 A2 | 11/2004 |
| WO | 05019906 A1 | 3/2005 |
| WO | 2005079546 A2 | 9/2005 |
| WO | 06025726 A1 | 3/2006 |
| WO | 2006032263 A2 | 3/2006 |
| WO | 2006047698 A1 | 5/2006 |
| WO | 06060477 A2 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2007142981 A2 | 12/2007 |
| WO | 2008045847 A2 | 4/2008 |
| WO | 2008083283 A2 | 7/2008 |
| WO | 2009020963 A1 | 2/2009 |
| WO | 2009029515 A1 | 3/2009 |
| WO | 2009076670 A1 | 6/2009 |
| WO | 2009105567 A1 | 8/2009 |
| WO | 2009137491 A1 | 11/2009 |
| WO | 2010009254 A1 | 1/2010 |
| WO | 2010009257 A1 | 1/2010 |
| WO | 2010028654 A1 | 3/2010 |
| WO | 2012052585 A1 | 4/2012 |
| WO | 2012074742 A1 | 6/2012 |
| WO | 2012083143 A1 | 6/2012 |
| WO | 2012085917 A1 | 6/2012 |
| WO | 2012154597 A1 | 11/2012 |
| WO | 2012166797 A1 | 12/2012 |
| WO | 2015022215 A1 | 2/2015 |
| WO | 2016032397 A1 | 3/2016 |
| WO | 2016087914 A1 | 6/2016 |
| WO | 2016123167 A1 | 8/2016 |

OTHER PUBLICATIONS

Abrahamsson M., et al., "Impairment of Contrast Sensitivity Function (CSF) as a Measure of Disability Glare," Investigative Ophthalmology & Visual Science, Jul. 1986, vol. 27 (7), pp. 1131-1136.

Alfonso J.F., et al., "Prospective Study of the Acri.LISA Bifocal Intraocular Lens," Journal of Cataract Refractive Surgery, Nov. 2007, vol. 33 (11), pp. 1930-1935.

Alio J.L., et al., "Phakic Anterior Chamber Lenses for the Correction of Myopia: A 7-Year Cumulative Analysis of Complications in 263 Cases," Ophthalmology, Mar. 1999, vol. 106 (3), pp. 458-466.

Apple D.J., et al., "Anterior Chamber Lenses Part 1: Complications and Pathology and a Review of Designs," Journal of Cataract Refractive Surgery, Mar. 1987, vol. 13 (2), pp. 157-174.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.

(56) References Cited

OTHER PUBLICATIONS

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.

Aslam, T.M., et al., "Development of a Forced Choice Photographic Questionnaire For Photic Phenomena and Its Testing—Repeatability, Reliability and Validity," Ophthalmologica, Nov.-Dec. 2004, vol. 218 (6), pp. 402-410.

Baikoff G., et al., "Angle-fixated Anterior Chamber Phakic Intraocular Lens for Myopia 7 to-19 Diopters," Journal of Refractive Surgery, May-Jun. 1998, vol. 14 (3), pp. 282-292.

Baumeister M., et al., "Tilt and Decentration of Spherical and Aspheric Intraocular Lenses: Effect on Higher-Order Aberrations," Journal of Cataract & Refractive Surgery, 2009, vol. 35 (6), pp. 1006-1012.

Beer J.M., et al., "Lasers' Spectral and Temporal Profile Can Affect Visual Glare Disability," Aviation, Space, and Environmental Medicine, Dec. 2012, vol. 83 (12), pp. 1135-1144.

Brainard D.H., The Psychophysics Toolbox, Spatial Vision, vol. 10, pp. 433-436.

Brown W.L., "Revisions to Tolerances in Cylinder Axis and in Progressive Addition Lens Power in ANSI Z80.1-2005," Optometry, 2006, vol. 77 (7), pp. 343-349.

Calatayud A., et al., "Imaging Quality of Multifocal Intraocular Lenses: Automated Assessment Setup," Ophthalmic and Physiological Optics, Jul. 2013, vol. 33 (4), pp. 420-426.

Canovas C., et al., "Customized Eye Models for Determining Optimized Intraocular Lenses Power," Biomedical Optics Express, Jun. 1, 2011, vol. 2 (6), pp. 1649-1662.

Canovas C., et al., "Hybrid Adaptive-Optics Visual Simulator," Optical Letters, Jan. 15, 2010, vol. 35 (2), pp. 196-198.

Cheng X., et al., "Predicting Subjective Judgment of Best Focus with Objective Image Quality Metrics," Journal of Vision, Apr. 2004, vol. 4 (4), pp. 310-321.

Cilco Advertisement Brochure, Oct. 1982, 3 pages.

Cohen A.L., "Practical Design of a Bifocal Hologram Contact Lens or Intraocular Lens," Applied Optics, Jul. 1, 1992, vol. 31 (19), pp. 3750-3754.

De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, Apr. 1992, vol. 1780, pp. 393-402.

Einighammer H.J., "The Individual Virtual Eye", Dissertation, 2008, 157 pages.

Fernandez E.J., et al., "Adaptive Optics Visual Simulator," Journal of Refractive Surgery, 2002, vol. 18 (5), pp. S634-S638.

Gobbi P.G., et al., "Far and Near Visual Acuity with Multifocal Intraocular Lenses in an Optomechanical Eye Model with Imaging Capability," Journal of Cataract and Refractive Surgery, 2007, vol. 33 (6), pp. 1082-1094.

Gobbi P.G., et al., "Optomechanical Eye Model with Imaging Capabilities for Objective Evaluation of Intraocular Lenses," Journal of Cataract and Refractive Surgery, 2006, vol. 32 (4), pp. 643-651.

Guirao A., et al., "Corneal Wave Aberration from Videokeratography: Accuracy And Limitations of the Procedure," Journal of the Optical Society of America, 2000, vol. 17 (6), pp. 955-965.

Hill W., et al., "Monte Carlo Simulation of Expected Outcomes with the Acrysof Toric Intraocular Lens," BMC Ophthalmology, Oct. 2008, vol. 8, pp. 22.

Jaeken B., et al., "Peripheral Aberrations in the Human Eye for Different Wavelengths: Off-Axis Chromatic Aberration," Journal of the Optical Society of America A, Sep. 2011, vol. 28 (9), pp. 1871-1879.

Javitt J.C., et al., "Validity and Reliability of the Cataract TyPE Spec: an Instrument For Measuring Outcomes of Cataract Extraction," American Journal of Ophthalmology, Aug. 2003, vol. 136 (2), pp. 285-290.

Jendritza B.B., et al., "Wavefront-Guided Excimer Laser Vision Correction after Multifocal IOL Implantation," Journal of Refractive Surgery, Mar. 2008, vol. 24 (3), pp. 274-279.

Johnson C.A., "Psychophysical Factors that Have Been Applied to Clinical Perimetry," Vision Research, Sep. 2013, vol. 90, pp. 25-31.

Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.

Kim M.J., et al., "Objective Evaluation of Through-Focus Optical Performance of Presbyopia-Correcting Intraocular Lenses Using an Optical Bench System," Journal of Cataract and Refractive Surgery, 2011, vol. 37 (7), pp. 1305-1312.

Klein S.A., "Optimal Corneal Ablation for Eyes with Arbitrary Hartmann-Shack Aberrations," Journal of the Optical Society of America A, 1998, vol. 15 (9), pp. 2580-2588.

Lesmes L.A., et al., "Bayesian Adaptive Estimation of the Contrast Sensitivity Function: the Quick CSF Method,"Journal of Vision, Mar. 2010, vol. 10 (3) 17, pp. 1-21.

Liang J., et al., "Objective Measurement Of Wave Aberrations Of The Human Eye With The Use Of A Hartmann-Shack Wave-Front Sensor," Journal of the Optical Society of America, 1994, vol. 11 (7), pp. 1949-1957.

Liou H.L., et al., "Anatomically Accurate, Finite Model Eye for Optical Modeling," Journal of Optical Society of America, Aug. 1997, vol. 14 (8), pp. 1684-1695.

Liou H.L., et al., "The Prediction of Spherical Aberration with Schematic Eyes," Ophthalmic and Physiological Optics, Jan. 1996, vol. 16 (4), pp. 348-354.

Marinho A., "Results are Encouraging for Phakic IOLs, but More Work is needed," Refractive Surgery, Feb. 2000, p. 12, 15.

Marsack J.D., et al., "Metrics of Optical Quality Derived from Wave Aberrations Predict Visual Performance," Journal of Vision, Apr. 2004, vol. 4 (4), pp. 322-328.

Menapace R., "The Capsular Tension Rings," Journal of Cataract & Refractive Surgery, Dec. 10, 2008, Chap. 3, pp. 27-44.

Mencucci R., et al., "Clinical outcomes and rotational stability of a 4-haptic toric intraocular lens in myopic eyes," Journal of Cataract & Refractive Surgery, Sep. 2014, vol. 40 (9), pp. 1479-1487.

Monsoriu J.A., et al., "Devil's Lenses," Optics Express, Oct. 17, 2007, vol. 15 (21), pp. 13858-13864.

Morlock, R., et al., "Patient-Reported Spectacle Independence Questionnaire (PRSIQ): Development and Validation,"American Journal of Ophthalmology, Jun. 2017, vol. 178, pp. 101-114.

Navarro R., et al., "Accommodation-Dependent Model of the Human Eye with Aspherics," Journal of the Optical Society of America, Aug. 1985, vol. 2 (8), pp. 1273-1281.

Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.

Norrby S., et al., "Model Eyes for Evaluation of Intraocular Lenses," Applied Optics, Sep. 7, 2007, vol. 46 (26), pp. 6595-6605.

Olsen T., "Simple Method to Calculate the Surgically Induced Refractive Change," Journal of Cataract & Refractive Surgery, Mar. 1993, vol. 19 (2), pp. 319-320.

Ortiz, C., et al., "Quantification and Monitoring of Visual Disturbances for patients with cataracts using Halo v1.0 software," Department of Optics, Laboratory of Vision Sciences and Applications, University of Granada, IWBBIO 2013, Mar. 20, 2013, XP055596332, Proceedings, 8 Pages.

Peli E., et al., "Appearance of Images Through A Multifocal Intraocular Lens," Journal of the Optical Society of America, 2001, vol. 18 (2), pp. 302-309.

Piers P.A., et al., "Eye Models for the Prediction of Contrast Vision in Patients with New Intraocular Lens Designs," Optics Letters, Apr. 1, 2004, vol. 29 (7), pp. 733-735.

(56) References Cited

OTHER PUBLICATIONS

Piers P.A., et al., "Theoretical Comparison of Aberration-Correcting Customized and Aspheric Intraocular Lenses," Journal of Refractive Surgery, Apr. 2007, vol. 23 (4), pp. 374-384.
Praeger D.L., "Praeger Technique for the Insertion of the Copeland Radial IOL Posterior Chamber Placement," Copeland Lens, 1982, 7 pages.
Rosen R.,et al., "A Bayesian Method Using through Focus Visual Acuity to Predict Rates of Spectacle Wear for Pseudophakic patients," Investigative Ophthalmology & Visual Science, Jul. 2018, vol. 59 (9), pp. 1075, ARVO Annual Meeting Abstract, Retrieved from the Internet: (URL: https://iovs.arvojournals.org/article.aspx?articleid=2693341&resultClick=1).
Siedlecki D., et al., "Radial Gradient index Intraocular Lens: a Theoretical Model," Journal of Modern Optics, Feb. 20-Mar. 10, 2008, vol. 55 (4-5), pp. 639-647.
Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.
Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Vass C., et al., "Prediction of Pseudophakic Capsular bag Diameter based on Biometric Variables," Journal of Cataract and Refractive Surgery, Oct. 1999, vol. 25 (10), pp. 1376-1381.
Villegas E.A., et al., "Correlation between Optical and Psychophy, Sical Parameters as a Function of Defocus," Optometry and Vision Science, Jan. 1, 2002, vol. 79 (1), pp. 60-67.
Vitale S., et al., "The Refractive Status and Vision Profile: A Questionnaire to Measure Vision-Related Quality of Life in Persons with Refractive Error," Ophthalmology, Aug. 2000, vol. 107 (8), pp. 1529-1539.
Weeber H.A., et al., "Influence of Corneal Aberrations on Dysphotopsia with Multifocal IOLs," ARVO, 2011, Abstract.
Weeber H.A., et al., "Influence of Corneal Aberrations on Dysphotopsia with Multifocal IOLs," RD3115, 2011.
Weeber H.A., et al., "Optical and Visual Performance of Patient Populations Implanted with Monofocal and Multifocal IOLs in the Presence of Defocus," Investigative Ophthalmology & Visual Science, 2010, vol. 51, E-Abstract 5751.
Weeber H.A., et al., "Population-based Visual Acuity in the Presence of Defocus Well Predicted By Classical Theory," Journal of Biomedical Optics, 2010, vol. 15 (4), pp. 040509.
Weeber H.A., et al., "Theoretical Performance of Intraocular Lenses Correcting Both Spherical and Chromatic Aberration," Journal of Refractive Surgery, 2012, vol. 28 (1), pp. 48-52.

\* cited by examiner

METHODS AND SYSTEMS FOR MEASURING IMAGE QUALITY

CROSS-REFERENCE TO RELATED APPLICATIONS

This application claims priority to and is a divisional of U.S. patent application Ser. No. 15/927,518, filed on Mar. 21, 2018, which claims the benefit of U.S. Provisional Patent Application No. 62/475,778, filed Mar. 23, 2017, all of which are incorporated herein by reference in their entirety.

TECHNICAL FIELD

This disclosure relates to method and system for intraocular lens (IOL) image quality, and more particularly to measurement of asymmetrical features.

BACKGROUND

Ophthalmic lenses, such as spectacles, contact lenses and intraocular lenses, may be configured to provide both spherical and cylindrical power. An intraocular lens (IOL) is a lens implanted in the eye used to treat cataracts or myopia. IOLs may b e used for restoring visual performance after a cataract surgery or other ophthalmic procedure in which the natural crystalline lens is replaced with or supplemented by implantation of an IOL. A variety of different types of IOLs are currently available, including monofocal and multifocal IOLs, phakic IOLs and piggyback IOLs (i.e. IOLs implanted in an eye already having an IOL).

Toric lenses typically have at least one surface that can be described by an asymmetric toric shape having two different primary curvature values in two orthogonal axes, wherein the toric lens is characterized by a "low power meridian" with a constant power equal to the base spherical power and an orthogonal "high power meridian" with a constant power equal to the base spherical power plus the cylinder power of the lens. Intraocular lenses, which are used to replace or supplement the natural lens of an eye, may also be configured to have a cylinder power for reducing or correcting the astigmatic effect of the cornea or eye.

One significant issue is the cost and/or time needed to develop and evaluate new IOL designs. Current methods and systems for measuring IOL image quality includes modular transfer function (MTF) measurement using an MTF bench for measuring the optical transfer function by its module and phase of an IOL. The MTF is the modulation or contrast of the image formed by the system or IOL for various spatial frequencies or various size targets. Frequently, black and white bars with 100% contrast are used as the targets. As the size of the target decreases, the system's ability to maintain high contrast decreases.

Such an MTF bench is typically used to measure the image quality with symmetrical features. That is, the modular transfer function is radially symmetrical. For an asymmetrical image quality like a toric lens, the MTF bench measures the X and Y meridians of the lens individually by forcing the image being evaluated be aligned with an X or Y meridian.

This may not be convenient and accurate enough to reflect the true image quality, especially in asymmetrical lenses, such as an IOL that may provide such as a highly asymmetric IOL or freeform design like the toric IOL with extended tolerance of astigmatic effects.

Therefore measuring the image quality by the current system design is not enough to capture the best image quality of the system (such an eye). Therefore, a method and system that can measure the meridian dependent image quality is needed to objectively and fully evaluate the image quality of asymmetrical IOLs including asymmetrical toric IOLs like extended tolerance astigmatism ("ETA") IOLs. Examples of such ETA IOLs are described in U.S. Patent Application No. 63/312,321 (filed Mar. 23, 2016); 63/312, 338 (filed Mar. 23, 2016); and 62/363,428 (filed Jul. 18, 2016), which are each hereby incorporated by reference for all purposes as if fully set forth herein.

SUMMARY

Accordingly, the present invention is directed to a method and system for measuring image quality by spatially varying MTF test that obviates one or more of the problems due to limitations and disadvantages of the related art.

An advantage of the present invention is to provide a method for evaluating performance of an intraocular lens, comprising: providing an image capture device, such as a charge coupled device (CCD), CMOS, film/light recording material, or any camera, in an initial start position with respect to an ophthalmic device such as an intraocular lens (IOL), toric intraocular lens or the like being measured; capturing a first image; changing a relative angular position of the CCD with respect to the IOL; capturing second image; and determining a measure of intraocular lens performance based upon the captured images. Another aspect of the present invention provides a method for evaluating performance of an intraocular lens, comprising: providing a charge coupled device (CCD) in an initial start position with respect to an intraocular lens (IOL) being measured, wherein the initial start position includes an initial angular position and an initial z-axis position; capturing a first image; repeatedly changing the relative angular position of the CCD with respect to the IOL and capturing images until the relative angular position of the CCD with respect to the IOL reaches a predetermined angular stop position; changing a relative z-axis position of the IOL with respect to the CCD and resetting the relative angular position of the CCD with respect to the IOL to the initial angular start position; repeatedly changing the relative angular position of the CCD with respect to the IOL and capturing images until the relative angular position of the CCD with respect to the IOL reaches the predetermined angular stop position; repeatedly changing the relative z-axis position of the IOL with respect to the CCD and capturing images until the relative z-axis position of the IOL with respect to the CCD reaches a predetermined z-axis stop position; and determining a measure of intraocular lens performance based upon the captured images.

The details of one or more embodiments of the disclosure are set forth in the accompanying drawings and the description below. Other features, objects, and advantages of the disclosure will be apparent from the description and drawings, and from the claims.

It is to be understood that both the foregoing general description and the following detailed description are exemplary and explanatory only, and are not restrictive of the invention as claimed.

DESCRIPTION OF DRAWINGS

The accompanying figures, which are incorporated herein and form part of the specification, illustrate methods and systems for measuring image quality. Together with the description, the figures further serve to explain the principles of the methods and systems for measuring image quality described herein and thereby enable a person skilled in the pertinent art to make and use the methods and systems for measuring asymmetrical image quality.

DETAILED DESCRIPTION

Reference will now be made in detail to embodiments of the an improved system and method for measuring meridian-dependent image quality with reference to the accompanying figures, in which like reference numerals indicate like elements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Because the functions of such a toric IOL usually works with a matching null lens to mimic an asymmetric eye model, an MTF bench that measures by alignment with an X or Y meridian will not accurately measure the asymmetric features. Like MTF that asymmetrical image quality is not only dependent on the best focus (defocus term), but also on the meridians or symmetry like the astigmatism of the optics under test.

For example, a regular toric IOL is designed to correct the astigmatic effect caused by the corneal astigmatism or cylindrical power with matching exactly the cylinder axis. If the cylindrical power axis were mismatched by 1 degree, there would b e about 3% reduction of the effectiveness of correction. If there were a 10 degrees misalignment, there would be about 35% reduction of such effectiveness of correction. The residual meridian power can be expressed as:

$$OC = 2*SIN(Alpha)*C/2*0.7*COS[2*(theta+90+Alpha)/2]$$

Where C is the astigmatic power at the IOL plane to be corrected at meridian theta and the Alpha is the misalignment of the cylindrical power axis.

Figure 1:
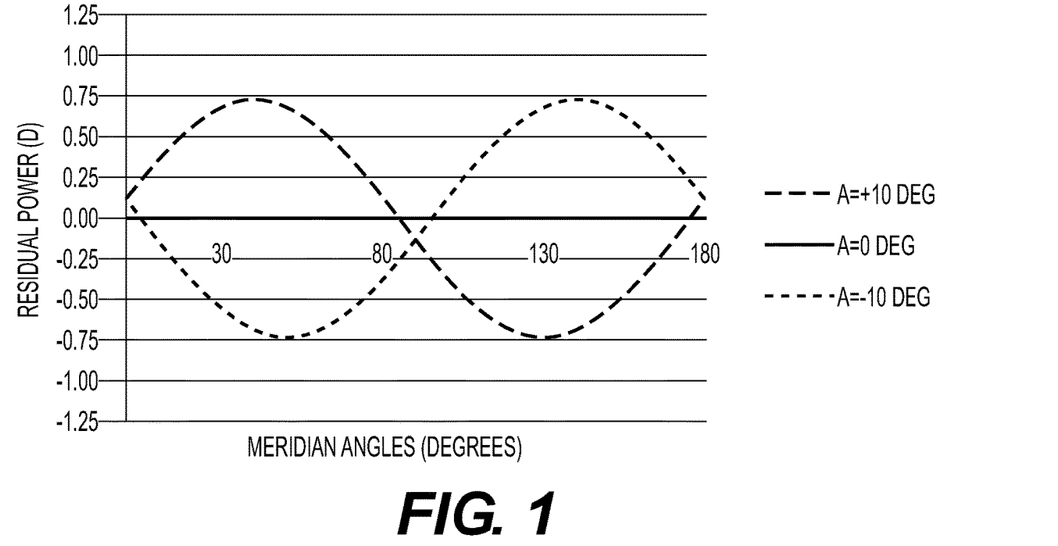
FIG. 1 is a (or depicts one embodiment of), for an example using a ZCT600 toric IOL for correcting a corneal astigmatic power of about 4.2D with 0 degree cylindrical axis, the residual cylinder for −10, 0, and 10 degrees misalignment.

For an example using a ZCT600 toric IOL for correcting a corneal astigmatic power of about 4.2D with 0 degree cylindrical axis, the residual cylinder for −10, 0, and 10 degrees misalignment is shown as in FIG. 1. As can be seen, the best image meridian is not along the X or Y axis orientation any longer. For this specific example alone, meridians 45+Alpha/2 and 135+Alpha/2 respectively. In addition, this also indicates that at alternative 45 and 135 degree meridian angles the Visual Acuity (VA), if the system were used for clinical use, may reflect the optimal than other meridians at best focus, but may not be reflected so if measures the X or Y meridian only. All meridians could be measured by this method.

Figure 2:
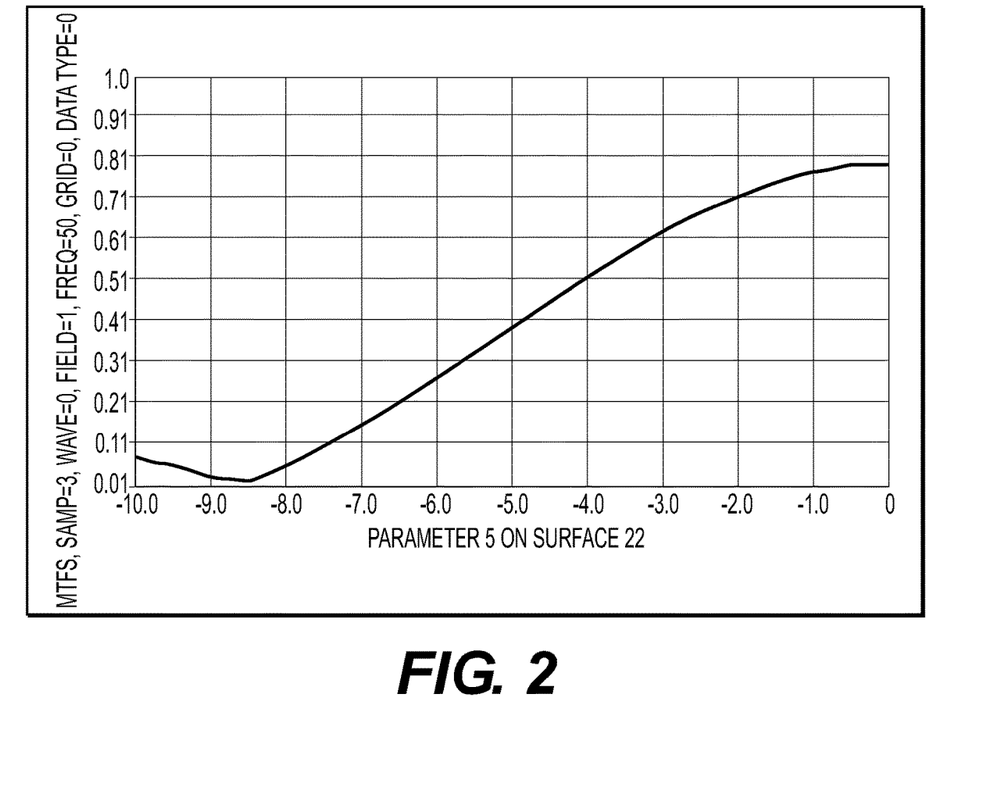
FIG. 2 illustrates measurement with X or Y only image quality by a current MTF bench with a CAM being zero and not zero for a regular toric IOL with 4.0D cylinder with a null astigmatic lens in an eye model.

Referring to FIG. 2, a regular toric IOL with 4.0D cylinder with a null lens in an eye model is used to illustrate the measurement with X or Y only image quality by a current MTF bench with a cylindrical axis misalignment (CAM) being zero and not zero (up to 10 degrees). As it can be seen that the measured MTF values are very low at the given clinically relevant CAM values. It does not reflect the best MTF possible due to the reasons described. In order to improve image quality measurement for asymmetrical lenses, one may consider the following options, but not limited to, to achieve during the test: The object (pinhole, slit, are force target etc.) be angularly modulated or changed; the optic system under test be angularly modulated or changed; the detector (system), image capture device, such as a CCD angularly modulated or changed. Any image capture device, such as CMOS, film/light recording material, any camera, or the like could be used in place of the CCD. The image processing and the image quality calculation algorithm includes the meridian variable, in other words, the X or Y can be angularly modulated or changed.

A solution according to principles of the present invention measures the modular transfer function through-focus and meridian (Through-Focus and Meridian Response) to evaluate image quality in the lens. Measuring the MTF through focus gives the best focus position and measuring the MRF through meridian gives the optimal meridian angle that reflects the best image quality, here the MTF values.

Figure 3A:
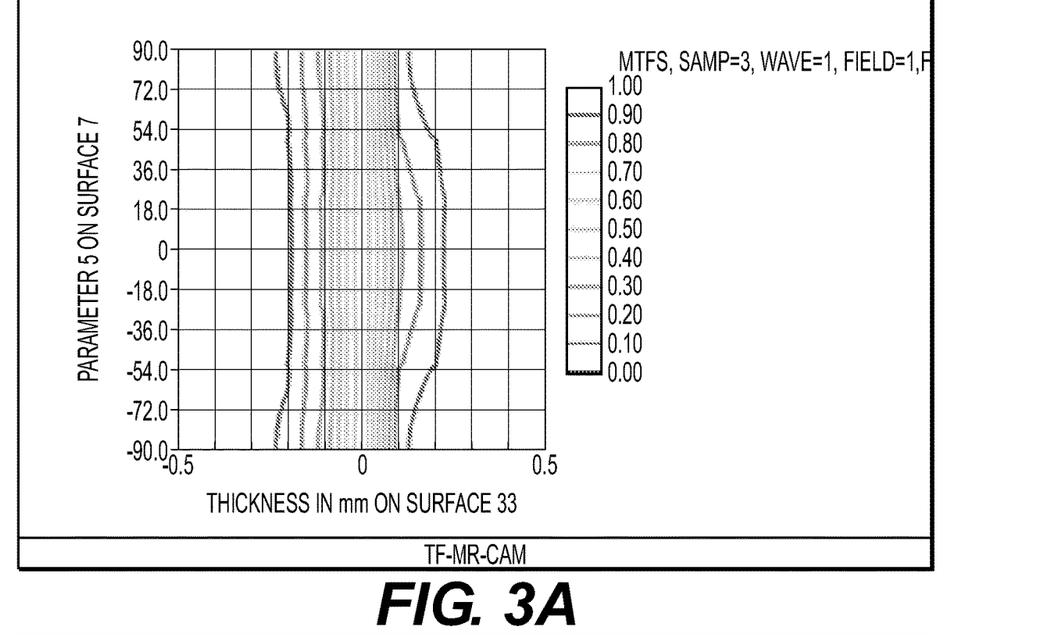
FIG. 3A illustrates Through-Focus and Meridian Response (TFMR) of a tonic IOL with 4.0D cylinder in an eye model with a null astigmatic lens when CAM=0.
Figure 3B:
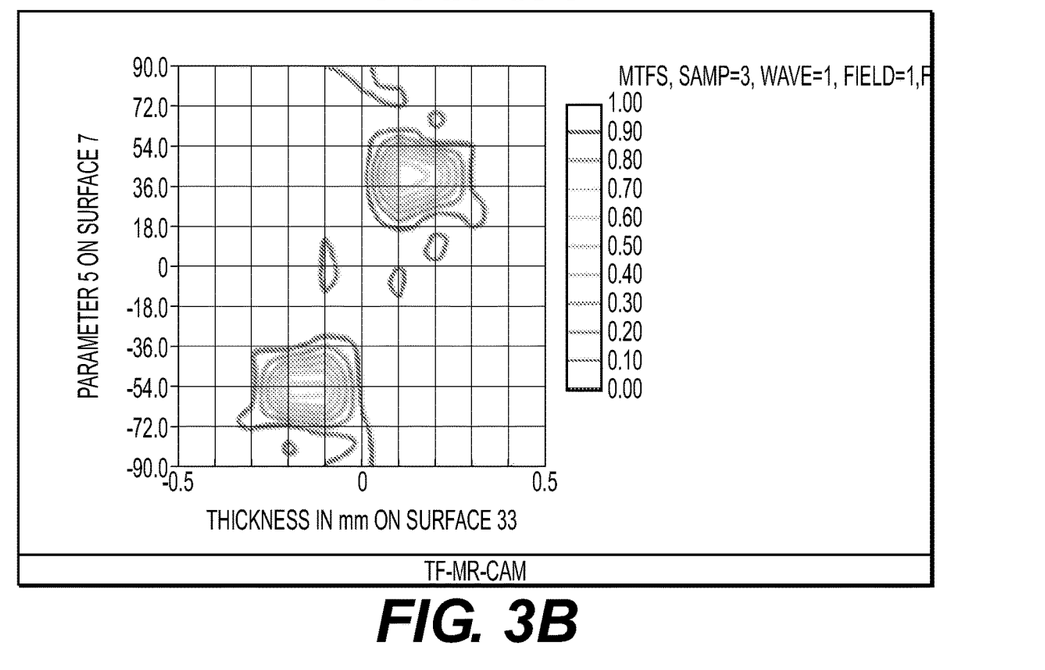
FIG. 3B illustrates Through-Focus and Meridian Response (TFMR) of a toric IOL with 4.0D cylinder in an eye model with a null astigmatic lens when CAM=10.

According to principles of the present invention, the image capture device or CCD used to measure IOL performance can be rotated to evaluate the IOL at predetermined CAM angles such that the various meridian responses can be measured, whereas conventional measurements are conducted only at a single meridian (or CCD position), typically 0 degrees. Such comparison is illustrated in FIGS. 3A and 3B. FIGS. 3A and B illustrate Through Focus and Meridian Response (MTF) of a toric IOL with 4.0D cylinder in an eye model with a null astigmatic lens when (a) CAM=0 degrees and (b) CAM=10 degrees. For the same case of using the IOL with 4.0D cylinder with a null lens in an eye model, FIGS. 3A and 3B illustrates the measured 3D image quality or MTF values in a contour format.

FIG. 3A illustrates measurement of the axis focal plane only at 0 degrees. The best MTF values illustrated in FIG. 3A center on the 0 mm depth. However, once the CCD is rotated, it can be shown that the best MTF performance of the sample IOL is not at 0 degrees, but instead at roughly −45 degrees and roughly +45 degrees.

As it can be seen that for any given CAM value, the measured 3D MTF value accurately reflects the optimal image quality of the toric IOL under test, although the best MTF values was not captured alone X or Y orientation. In addition, the measured TFMR also, if validated, can give the residual astigmatic and sphere equivalent powers simultaneously. If the Null lens is free of any power or non-existed, the measured would be the astigmatism power and spherical equivalent powers of the IOL.

Rotating the CCD as described above does not provide information as to the best focal plane of the IOL. Thus, additional focal plane information should be determined. That is, focal plane can be varied and tested by moving the location of the CCD with respect to the lens such that the lens is measured in both CAM and meridian response.

In an embodiment of the present system and method, an initial start focal plane position of the IOL is determined and an end focal plane position is determined. An initial CCD rotation angle is determined and an end CCD rotation angle is determined. The CCD and the IOL are placed in proper relative position. Measurements are taken at the initial rotation angle and initial focal plane position of the CCD. After initial measurement, the rotation angle or the focal plane position are incremented and additional measurements taken. The rotation angle may be incremented by rotating the physical CCD, rotating a stage hosting the CCD, or rotating the IOL or a stage or holder hosting the IOL to change the relative angular position of the CCD with respect to the IOL. According the principles of the present embodiment, the relative rotation angle is incremented by 1 degree, but may be incremented at 0.5 degrees or as the resolution of the CCD will allow. The focal plane position may be incremented by moving the physical CCD or a stage hosting the CCD, or moving the IOL or the stage or holder hosting the IOL to change the relative focal plane depth of the IOL with respect to the CCD. According the principles of the present embodiment, the relative focal plane position is incremented by 0.02 mm (20 microns), but may be incremented at 0.01 mm (10 microns) or as the resolution of the CCD will allow. That is, the following is measured or tracked: 1) movement of the CCD in Z; 2) rotation of IOL or detector (CCD); 3) rotation of the sample window; 4) rotation of patterned/featured object/etc.

Figure 4:
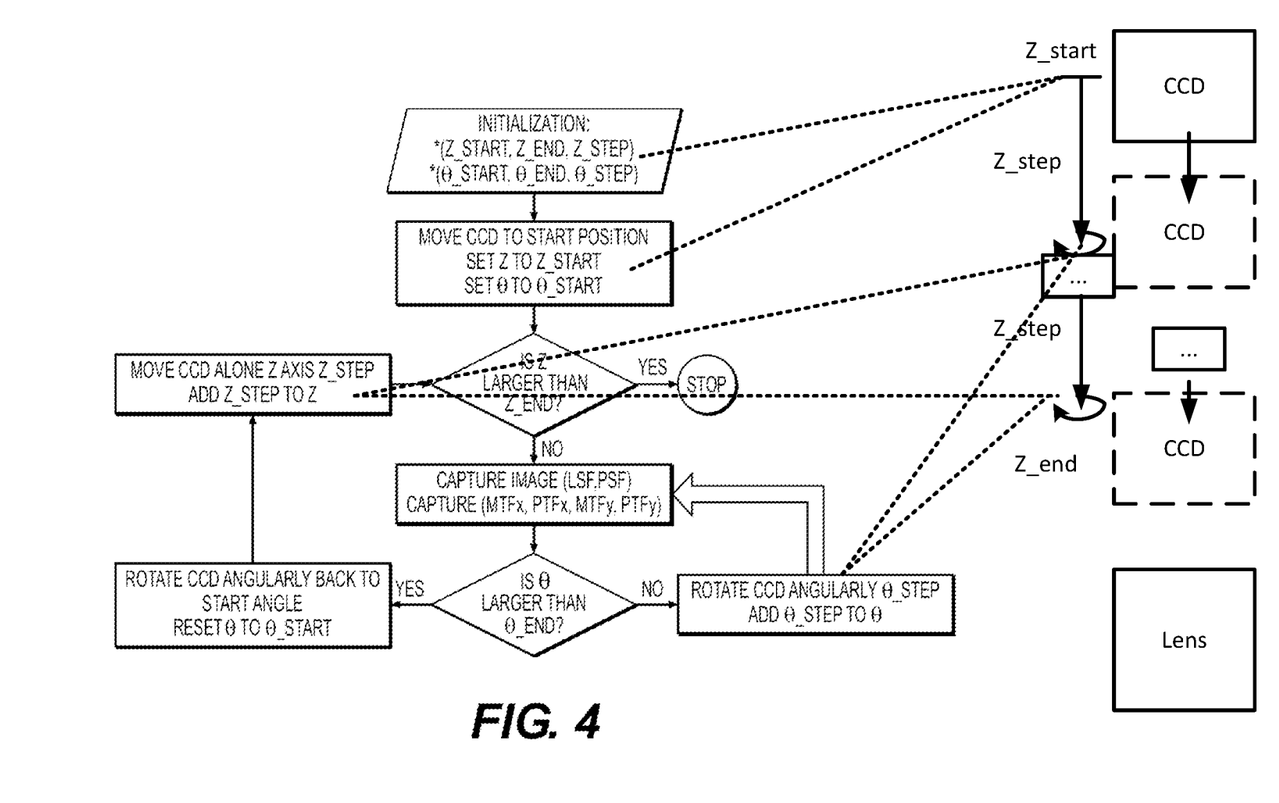
FIG. 4 illustrates a flow diagram according to principles of the present invention for a rotating CCD using a rotational stage.

A method and system for rotating the CCD using a rotational stage over 180 degrees in 1 degree increments/resolution is illustrated in the flow chart of FIG. 4. A system for implementing the method includes, e.g., a typical bench illustration: light source, target, (optional) collimator, (optional) null lens, eye model (ACE/ISO), relay system, detector (microscope+CCD system or S-H system. As illustrated in the flow chart, z_start, z_end and z_step are provided, where z_start is the initial focal plane measurement position of the IOL relative to the CCD, z_end is the end focal plane measurement position of the IOL relative to the CCD, and z_step is the increment between focal plane measurement positions of the IOL relative to the CCD. As illustrated in the flow chart, $\theta$_start, $\theta$_end and $\theta$_step are provided, where $\theta$_start is the initial relative rotation angle of the CCD relative to the IOL, $\theta$_end is the end relative rotation angle of the CCD relative to the IOL, and $\theta$_step is the increment between measurement positions of the rotation angle of the CCD relative to the IOL. As long as the focal plane position is less than z_end, an image is captured by the CCD and, e.g., line spread function (LSF)/point spread function (PSF) and modular transfer function at the X/Y location and the point transfer function at the X/Y location are measured, plotted, recorded and/or the like for the particular location (rotation angle, X, Y). The value of the next measurement angle location $\theta$ is calculated. As long as the value of the next measurement angle location is less than $\theta$_end, the CCD (or its stage) is rotated by the appropriate increment $\theta$_step. If the value of the next measurement angle location $\theta$ is larger than $\theta$_step, then the next measurement angle returns to $\theta$_start by rotating the CCD (or its stage), and the relative position of the CCD and IOL is incremented to the next focal plane position by incrementing focal plane measurement position z by z_step. If the value of the focal plane measurement position z, having been incremented, is greater than z_end, then the measurement of the IOL by the CCD is concluded. Exemplary values for z_start, z_end and z_step are −2 mm, +2 mm and 0.02 mm, respectively. Exemplary values for $\theta$_start, $\theta$_end and $\theta$_step are −90 degrees, +90 degrees, and 1 degree, respectively. These values cover IOL cylindrical powers of about 22D.

Figure 5:
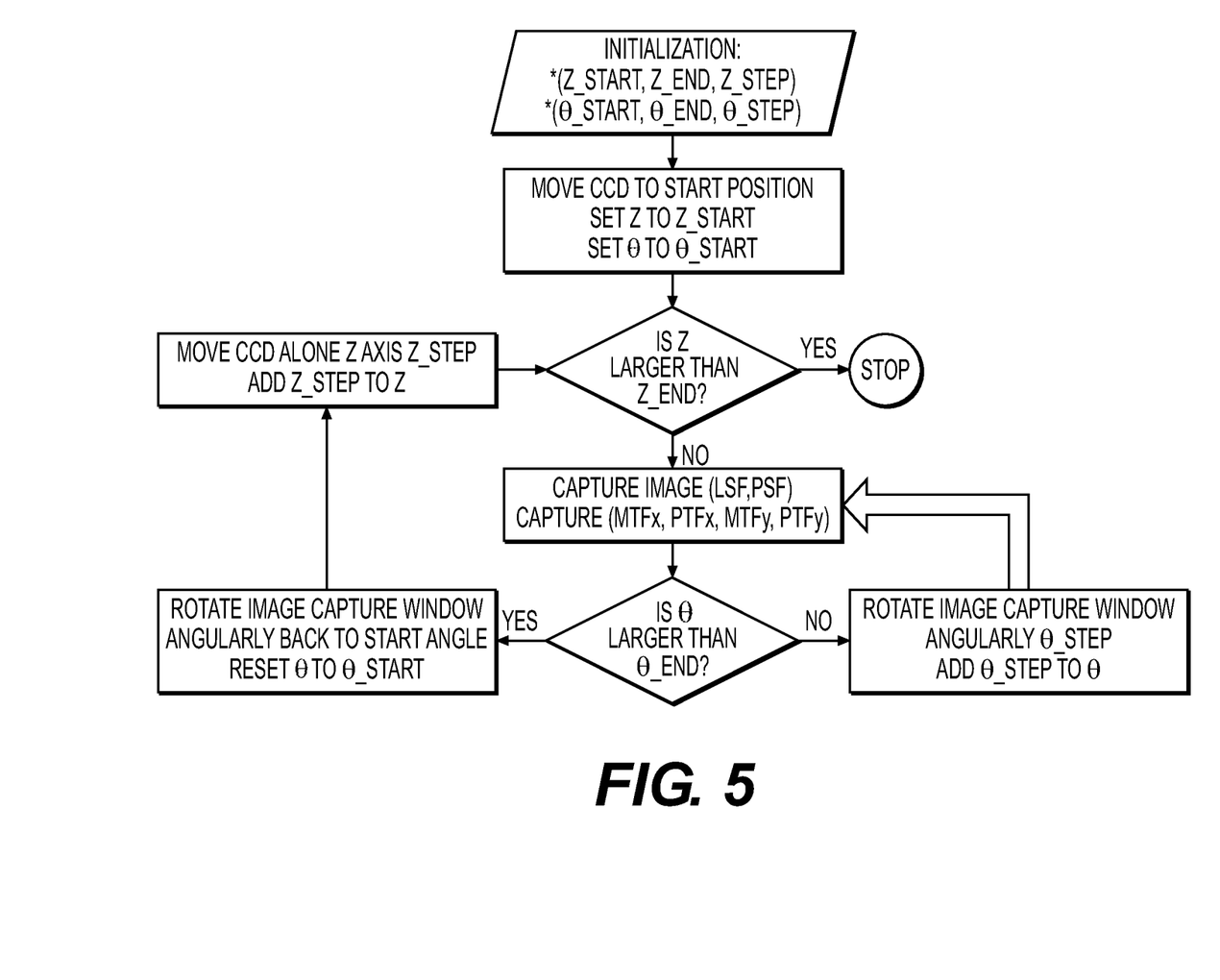
FIG. 5 illustrates a flow diagram according to principles of the present invention for modulating the X and Y axis in the image processing software.

Alternatively, as illustrated in FIG. 5, the X and Y axis in the image processing software without significantly changing any other hardware. E.g., rather than rotating the CCD itself or its stage to change the relative angular position of the CCD with respect to the IOL, an image capture window may be rotated appropriately according to the steps described above. As illustrated in the flow chart, z_start, z_end and z_step are provided, where z_start is the initial focal plane measurement position of the IOL relative to the CCD, z_end is the end focal plane measurement position of the IOL relative to the CCD, and z_step is the increment between focal plane measurement positions of the IOL relative to the CCD. As illustrated in the flow chart, $\theta$_start, $\theta$_end and $\theta$_step are provided, where $\theta$_start is the initial relative rotation angle of the CCD relative to the IOL, $\theta$_end is the end relative rotation angle of the CCD relative to the IOL, and $\theta$_step is the increment between measurement positions of the rotation angle of the CCD relative to the IOL. As long as the focal plane position is less than z_end, an image is captured by the CCD and, e.g., line spread function (LSF)/point spread function (PSF) and modular transfer function at the X/Y location and the point transfer function at the X/Y location are measured, plotted, recorded and/or the like for the particular location (rotation angle, X, Y). The value of the next measurement angle location $\theta$ is calculated. As long as the value of the next measurement angle location is less than $\theta$_end, the image capture window is rotated by the appropriate increment $\theta$_step. If the value of the next measurement angle location $\theta$ is larger than $\theta$_step, then the next measurement angle returns to $\theta$_start by rotating the image capture window relative to the IOL, and the relative position of the CCD and IOL is incremented to the next focal plane position by incrementing focal plane measurement position z by z_step. If the value of the focal plane measurement position z, having been incremented, is greater than z_end, then the measurement of the IOL by the CCD is concluded.

Figure 6:
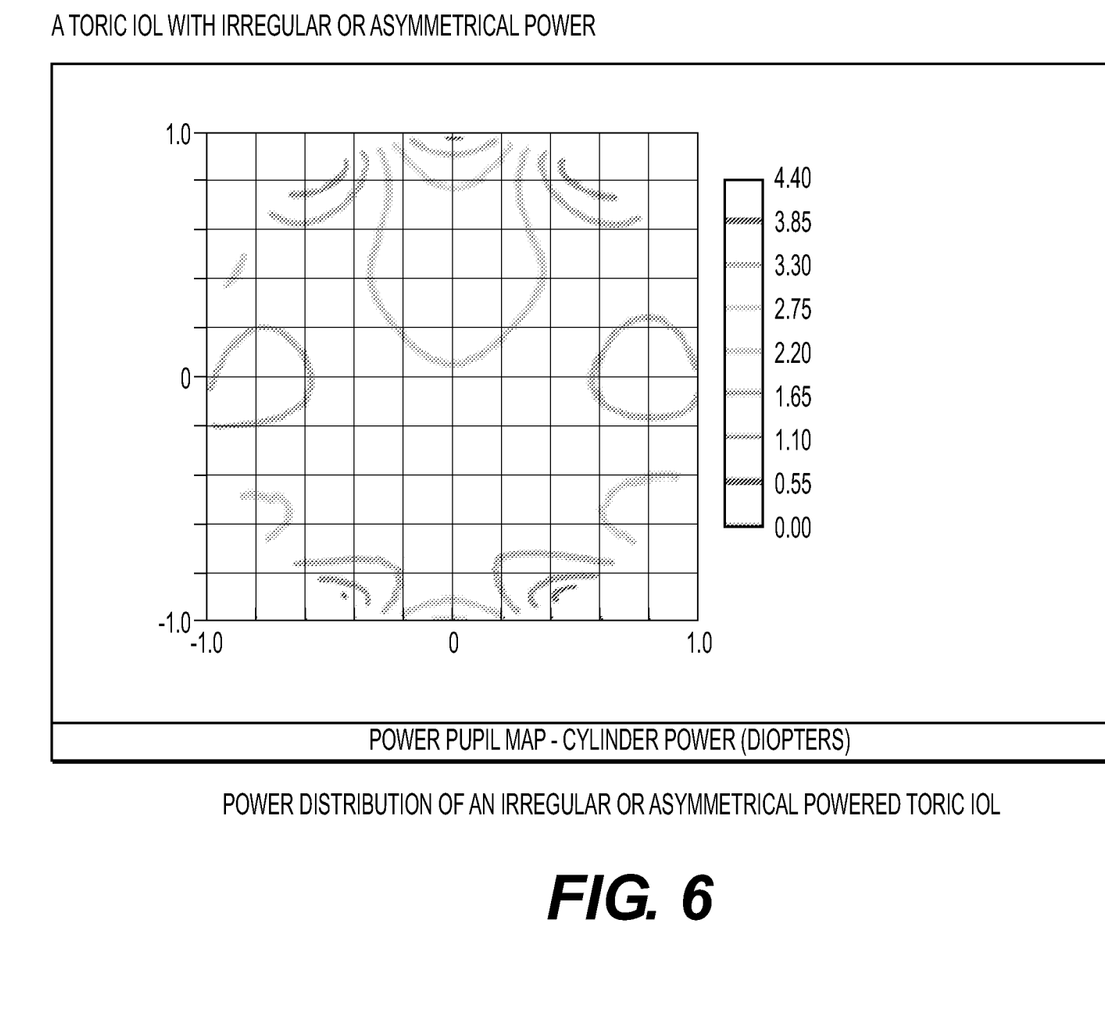
FIG. 6 shows measured MTF values using a known MTF bench for an irregular or asymmetrical-powered toric IOL
Figure 7A:
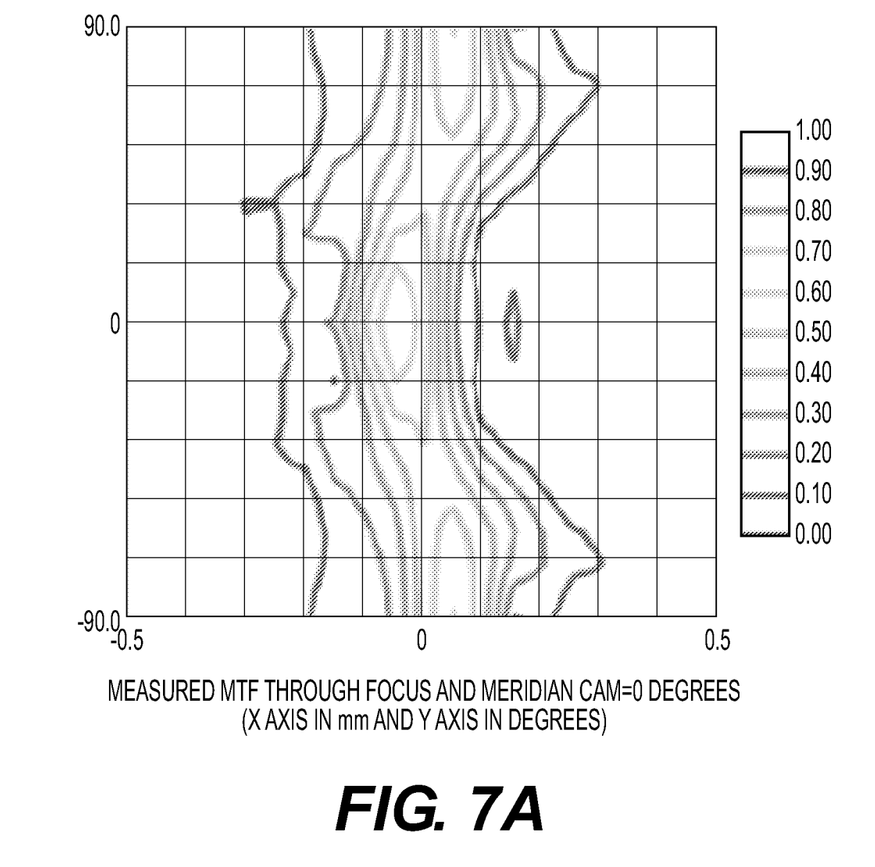
FIGS. 7A and 7B show measured MTF values using the disclosed bench with the TFMR.
Figure 7B:
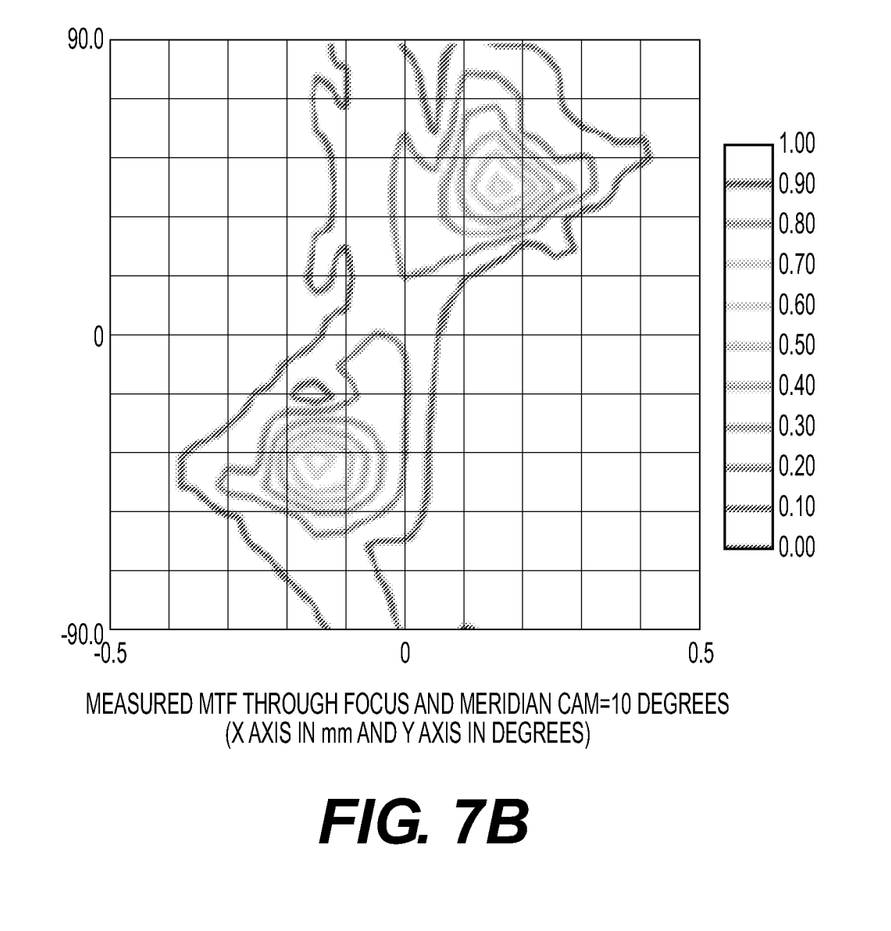

For another example, for an irregular or asymmetrical powered toric IOL, as shown in FIG. 6, the measured MTF values using a current MTF bench and the disclosed bench with the TFMR are shown in FIGS. 7a and b.

As it can be seen that the TFMR is obvious reflects the optimal image quality more in full of the irregular IOL.

The methods and system for measuring asymmetrical image quality is helpful measuring lens designs that can operate over a range of misalignments (e.g., +/−10 degrees of misalignment) as compared to conventional toric IOLs, which would work up to only +/−3 degrees. That is, aspects and embodiments described herein address the issue that prior art measurement devices cannot effectively measure performance of lens designs that operate over a range of misalignment, because prior art measurement devices do not take into account misalignment and point of focus of such an "ETA" lens, e.g. a lens with extended band operation (e.g., can work up to +/−10 degree of rotational error whereas current lens will not work if there is a +/−3 degree offset, for example). In addition, it can be appreciated the disclosed system and methods can be used to measure any type of lens, and is not limited to those that operate over a range of misalignments.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A method for evaluating performance of an intraocular lens, comprising:
   determining an initial start position with respect to an intraocular lens (IOL) being measured and providing a charge coupled device (CCD) in the initial start position, wherein the initial start position includes an initial angular position and an initial z-axis position;
   capturing a first image;
   repeatedly moving the relative angular position of the CCD with respect to the IOL from the initial start position and capturing subsequent images until the relative angular position of the CCD with respect to the IOL reaches a predetermined angular stop position;
   changing a relative z-axis position of the IOL with respect to the CCD and resetting the relative angular position of the CCD with respect to the IOL to the initial angular start position;
   repeatedly moving the relative angular position of the CCD with respect to the IOL and capturing subsequent images until the relative angular position of the CCD with respect to the IOL reaches the predetermined angular stop position;
   repeatedly moving the relative z-axis position of the IOL with respect to the CCD and capturing subsequent images until the relative z-axis position of the IOL with respect to the CCD reaches a predetermined z-axis stop position; and
   determining a measure of intraocular lens performance based upon the captured images.

2. The method of claim 1, wherein the changing of the relative z-axis position of the IOL with respect to the CCD comprises changing the relative z-axis position of the IOL with respect to the CCD by a predetermine distance.

3. The method of claim 1, wherein the predetermined distance is 0.01 mm.

4. The method of claim 1, wherein initial z-axis position is 2 mm and the z-axis stop position can be +2 mm.

5. The method of claim 1, wherein the changing of the relative angular position of the CCD with respect to the IOL comprises rotating the CCD relative to the IOL.

6. The method of claim 1, wherein the CCD is positioned on a stage and wherein changing of the relative angular position of the CCD with respect to the IOL comprises rotating the stage relative to the IOL.

7. The method of claim 1, wherein the changing of the relative angular position of the CCD with respect to the IOL comprises rotating an image capture window angularly.

8. The method of claim 1, wherein the changing of the relative angular position of the CCD with respect to the IOL comprises changing the relative angular position of the CCD with respect to the IOL by a predetermine angle.

9. The method of claim 8, wherein the predetermined angle is 1 degree.

10. The method of claim 1, wherein the predetermined angular stop position is 90 degrees relative angle of the CCD with respect to the IOL.

11. The method of claim 1, wherein the initial start angular position of the CCD is 90 degrees relative angle of the CCD with respect to the IOL.

* * * * *